United States Patent [19]
Schmidt

[11] Patent Number: 5,784,428
[45] Date of Patent: Jul. 21, 1998

[54] X-RAY COMPUTED TOMOGRAPHY APPARATUS HAVING A GANTRY FRAME WITH ROLLERS FOR AXIALLY AND RADIALLY GUIDING THE GANTRY

[75] Inventor: Martin Schmidt, Emskirchen, Germany

[73] Assignee: Siemens Aktiengesellschaft, Munich, Germany

[21] Appl. No.: 865,973

[22] Filed: May 30, 1997

[30] Foreign Application Priority Data

Jul. 24, 1996 [DE] Germany .................. 196 29 931.4

[51] Int. Cl.⁶ .................................................. G01N 23/00
[52] U.S. Cl. ............................... 378/4; 378/15; 378/17; 378/197
[58] Field of Search ............................. 378/4, 17, 15, 378/195–197

[56] References Cited

U.S. PATENT DOCUMENTS 4,916,718   4/1990   Manring.

Primary Examiner—Craig E. Church
Attorney, Agent, or Firm—Hill & Simpson

[57] ABSTRACT

An X-ray computed tomography apparatus has a gantry rotatably mounted in a frame for rotating an X-ray source, mounted on the gantry, around an examination subject disposed in a central opening in the gantry. The gantry has rails at an outer circumference thereof, and the frame has a first set of rollers engaging the rails for radially guiding the gantry and a second set of rollers engaging the rails for axially guiding the gantry.

6 Claims, 1 Drawing Sheet

X-RAY COMPUTED TOMOGRAPHY APPARATUS HAVING A GANTRY FRAME WITH ROLLERS FOR AXIALLY AND RADIALLY GUIDING THE GANTRY

BACKGROUND OF THE INVENTION

1. Field of the Invention

The present invention is directed to an X-ray computed tomography apparatus, and in particular to a tomography apparatus of the type having a gantry, on which at least an X-ray source is mounted, which rotates in a frame around an examination subject, the examination subject being received in a central opening in the gantry.

2. Description of the Prior Art

In general, a conventional X-ray computed tomography apparatus has a rotating frame, called a gantry, on which a source of X-rays and a beam detector are mounted. The X-ray radiation is gated in the shape of a beam, so that a layer of the examination subject is transilluminated from various directions during the rotation of the measurement unit consisting of the X-ray source and the beam detector. A computer calculates an image of the examination subject from the detector output signals, which image can be reproduced on a monitor.

For the rotation of the gantry, it is known to provide a ball bearing ring that externally surrounds the gantry and in which the gantry can be rotated. Oscillations can ensue with such a construction that can lead to an undesired development of noise. In addition, known computed tomography apparatuses are always constructed as a unit, i.e. mounting elements of one type cannot be used for another type.

SUMMARY OF THE INVENTION

An object of the present invention is to provide an X-ray computed tomograph with an annular, rotatably mounted gantry, on which at least the X-ray source is fastened, which is simplified in comparison to known systems with respect to the gantry mounting, and in particular which enables different gantry dimensions to be housed in one frame.

The above object is achieved in accordance with the principles of the present invention in a computed tomography apparatus having a frame with a gantry, carrying an X-ray source, rotatably mounted in the frame for rotating the X-ray source around an examination subject received in a central opening in the gantry, and wherein the gantry has rails at an outer circumference thereof, the rails engaging a first set of rollers mounted in the frame for radially guiding the gantry, and the rails also engaging a second set of rollers mounted in the frame for axially guiding the gantry.

In the computed tomography apparatus of the invention, a stationary frame is provided with at least three roller bearings that guide the gantry in the radial and axial directions on annular rails fastened to the gantry. It is thereby possible to mount gantries with different measurement opening diameters in one frame; i.e., one frame can be used for different types.

DESCRIPTION OF THE PREFERRED EMBODIMENTS

Figure 2:
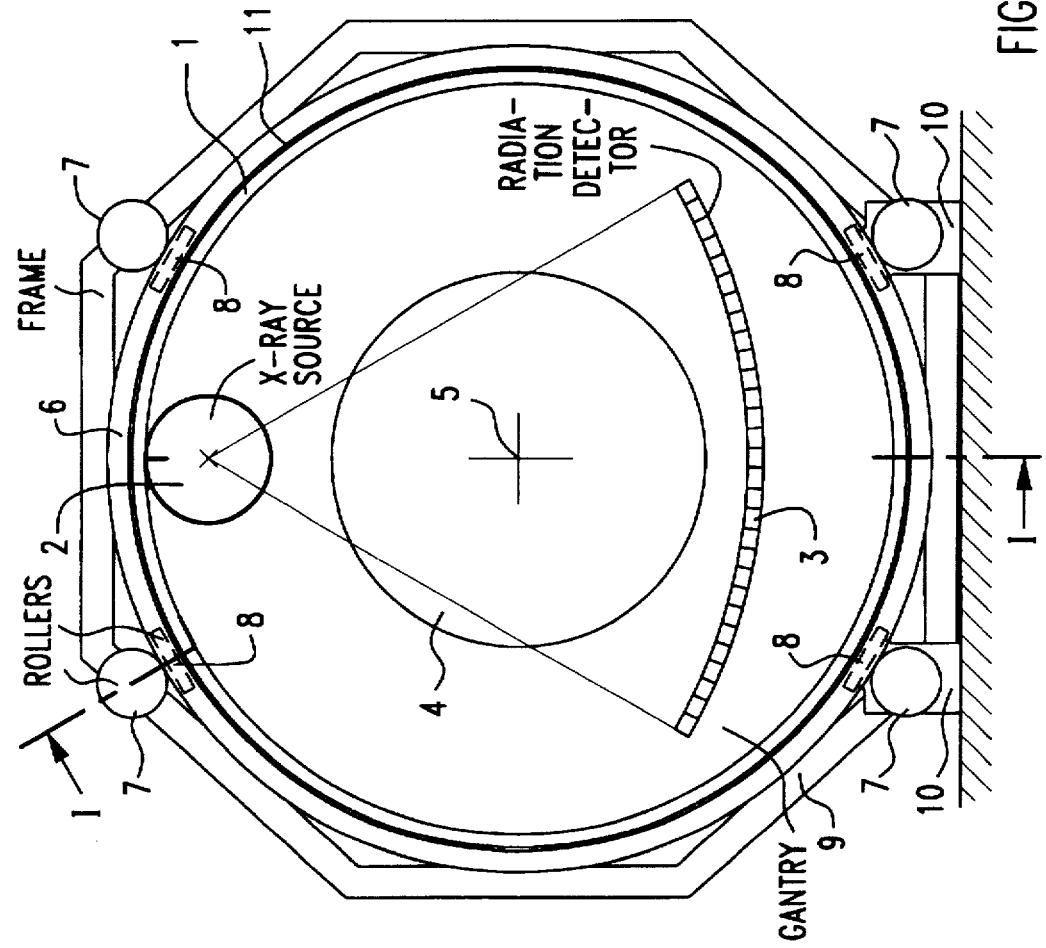
FIG. 2 is a front view of a computed tomography apparatus constructed in accordance with the principles of the present invention.
Figure 1:
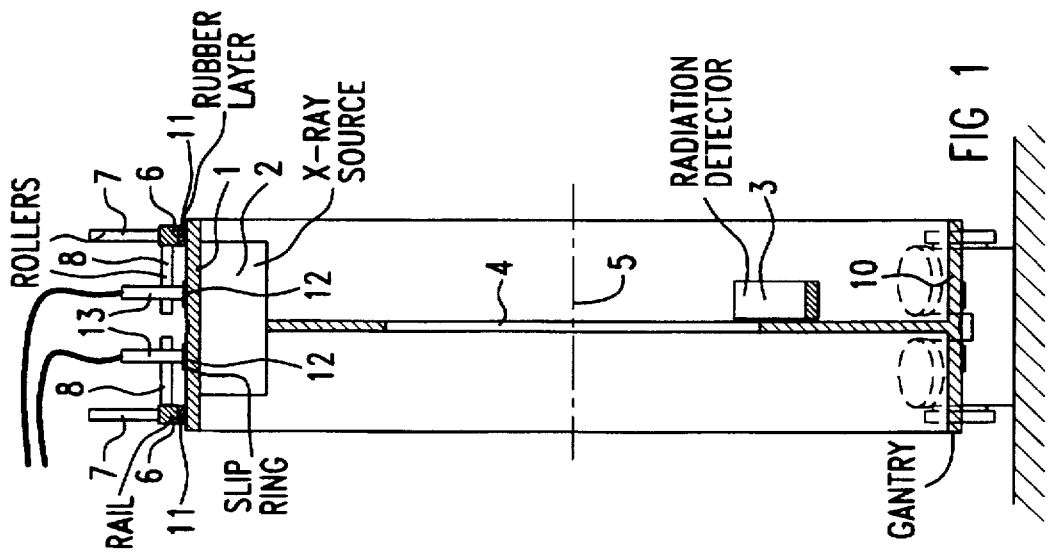
FIG. 1 is a sideview, partly in section, of a computed tomography apparatus constructed in accordance with the principles of the present invention, the view being taken along line I—I of FIG. 2.

FIGS. 1 and 2 show an annular gantry 1 on which an X-ray source 2 and a beam detector 3 are fastened. The beam detector 3 consists of a series of detector elements whose output signals are supplied in a known way to a computer for the calculation of an image of the subject under examination. The gantry 1 has a central opening 4 in which the examination subject is received. By rotating the gantry 1 around the system axis 5, the examination subject can be transilluminated from various directions by the X-ray beam that is emitted by the X-ray source 2, and which is gated in a fan shape.

The gantry 1 is provided on its exterior with two rails 6 on which rollers 7 and 8 run. The rollers 7 thereby guide the gantry 1 in the radial direction, and the rollers 8 in the axial direction. The rollers 7 and 8 are rotationally mounted on a frame 9 (not shown in FIG. 1), which surrounds the gantry 1 with the rails 6. The frame 9 is supported on the floor of the examination chamber by suitable supports.

For damping noise, the rails 6 are not connected with the gantry 1 directly, but rather with an intermediate connection of a layer of rubber 11. Slip rings 12 are arranged on the circumference of the gantry 1, on which brushes 13 ride that serve for supplying high voltage to the X-ray source 2. By means of this construction, a continuous rotation of the gantry 1 can be achieved with a relatively short construction of the overall computed tomography apparatus.

By means of the invention, a rigid drum solution with a balanced center of gravity position in the z direction (direction of the system axis 5) is achieved. The rails 6 and the slip rings 12 on the circumference of the drum-type gantry 1 enable a narrow construction. Standardized roller bearings can be used to mount the gantry 1. A high flexibility thereby results with respect to the diameter of the gantry opening.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray computed tomography apparatus comprising:

a frame;

an X-ray source and an X-ray detector;

an annular gantry on which at least said X-ray source is mounted, said annular gantry having a central opening for receiving an examination subject and being rotatably mounted in said frame for rotating said X-ray source around an examination subject in said opening, said gantry having an outer circumference with rails projecting from said outer circumference;

a first set of rollers in said frame engaging said rails for radially guiding said gantry; and a second set of rollers in said frame engaging said rails for axially guiding said gantry.

2. A computed tomography apparatus as claimed in claim 1 wherein each roller in said first set of rollers has a first rotational axis and wherein each roller in said second set of rollers has a second rotational axis, wherein said rails have first and second sides, and wherein said first and second axes are disposed perpendicularly relative to each other so that said first and second sets of rollers respectively ride on said first and second sides of said rails.

3. A computed tomography apparatus as claimed in claim 2 wherein said gantry has two annular rails on said circumference, and wherein said second set of rollers is disposed between said two rails.

4. A computed tomography apparatus as claimed in claim 1 further comprising a rubber layer disposed at said circumference of said gantry between said circumference and said rails.

5. A computed tomography apparatus as claimed in claim 1 further comprising annular slip rings on said circumference of said gantry for supplying high voltage to said X-ray source.

6. A computed tomography apparatus as claimed in claim 5 wherein said gantry has two rails and wherein said slip rings are disposed between said two rails.

* * * * *